US011345952B2

(12) United States Patent
Vranes et al.

(10) Patent No.: US 11,345,952 B2
(45) Date of Patent: May 31, 2022

(54) INTERNAL AMPLIFICATION CONTROL

(71) Applicant: QIAGEN GmbH, Hilden (DE)

(72) Inventors: Miroslav Vranes, Hilden (DE); Ralf Peist, Hilden (DE); Mario Scherer, Hilden (DE); Stefan Otto Cornelius, Hilden (DE)

(73) Assignee: Qiagen GmbH, Hilden (DE)

( * ) Notice: Subject to any disclaimer, the term of this patent is extended or adjusted under 35 U.S.C. 154(b) by 350 days.

(21) Appl. No.: 16/333,143

(22) PCT Filed: Sep. 15, 2017

(86) PCT No.: PCT/EP2017/073304

§ 371 (c)(1),
(2) Date: Mar. 13, 2019

(87) PCT Pub. No.: WO2018/050835

PCT Pub. Date: Mar. 22, 2018

(65) Prior Publication Data

US 2020/0087720 A1 Mar. 19, 2020

(30) Foreign Application Priority Data

Sep. 16, 2016 (EP) .................................... 16189225

(51) Int. Cl.
*C12Q 1/6851* (2018.01)
*C12Q 1/6844* (2018.01)
*C12Q 1/6848* (2018.01)

(52) U.S. Cl.
CPC ......... *C12Q 1/6846* (2013.01); *C12Q 1/6848* (2013.01); *C12Q 1/6851* (2013.01); *C12Q 2545/101* (2013.01); *C12Q 2600/166* (2013.01)

(58) Field of Classification Search
None
See application file for complete search history.

(56) References Cited

U.S. PATENT DOCUMENTS

2014/0147843 A1 5/2014 Di Pasquale et al.
2017/0002397 A1 1/2017 Strauss et al.

FOREIGN PATENT DOCUMENTS

WO 2012113577 A1 8/2012
WO 2015114009 A1 8/2015
WO WO-2015114009 A1 * 8/2015 ............ C12Q 1/686

OTHER PUBLICATIONS

Pennington, Dealing with Amplification Inhibitors: Reagent Choice Matters, Promega, Feb. 2014 webinar. (Year: 2014).*

International Search Report dated Nov. 6, 2017 filed in PCT/EP2017/073304.

M. Funes-Huacca et al. "A comparison of the effects of PCR inhibition in quantitative PCR and forensic STR analysis," Electrophoresis, Apr. 4, 2011, pp. 1084-1089, vol. 32 No. 9, Wiley-VCH Berlag GmbH & Co., Weinheim, Germany; Cited in International Search Report.

A. Pionzio et al. "The effect of internal control sequence and length of the response to PCR inhibition in real-time PCR quantitation," Forensic Science International: Genetics, 2014, pp. 55-60, vol. 9, Elsevier, The Netherlands Cited in ISR.

J. Thomas et al. "Qiagen's Investigator Quantiplex Kit as a Predictor of STR Amplification Success from Low-Yield DNA Samples,"Journal of Forensic Sciences, Sep. 2013, pp. 1306-1309, vol. 58 No. 5, American Academy of Forensic Sciences, US; Cited in ISR.

M. Scherer et al. "Improving sample analysis and interpretation using QIAGEN's latest Investigator STR multiplex PCR assays with a novel quality sensor," Forensic Science International: Genetics Supplement Series, 2015, pp. e308-e309, vol. 5, Elsevier Ireland Ltd., Ireland; Cited in ISR.

(Continued)

*Primary Examiner* — Samuel C Woolwine
*Assistant Examiner* — Carolyn L Greene
(74) *Attorney, Agent, or Firm* — Rankin, Hill & Clark LLP

(57) ABSTRACT

PCR that allows the researchers to amplify a desired DNA requiring only tiny amounts of sample. Such amplification reactions are technically challenging and are often hampered by several practical issues such as the presence of PCR inhibitors, sample degradation and low quantities of said sample. The invention addresses these issues with a method for evaluating the amplification efficiency and/or the presence of inhibitors and/or degradation and/or performing a quantification of a nucleic acid in a real-time amplification reaction comprising: optionally amplifying in a reaction composition a first target nucleic acid using a first primer pair in a real-time amplification reaction, (i) amplifying in said reaction composition one or more second internal nucleic acid control templates (IC) with a length of between 50 and 2000 nucleotides, wherein the second nucleic acid has a sequence selected from the group of: i) SEQ ID NO. 1 or a sequence that is differs by no more than 15% therefrom, ii) a reverse complement of SEQ ID NO. 1 or a sequence that is differs by no more than 15% therefrom, iii) a sequence or a reverse complement thereof comprising the final 18 to 30 3'-nucleotides of SEQ ID NO. 1 at its terminal 3'-end and the final 18 to 30 5'-nucleotides of SEQ ID NO. 1 at its terminal 5'-end, or terminal ends that differ by no more than 5% from SEQ ID NO. 1, wherein between these terminal 3'-ends and 5'-ends the nucleic may have any nucleotide sequence and is between about 30 and about 1950 nucleotides in length.

6 Claims, 3 Drawing Sheets

Figure 1:
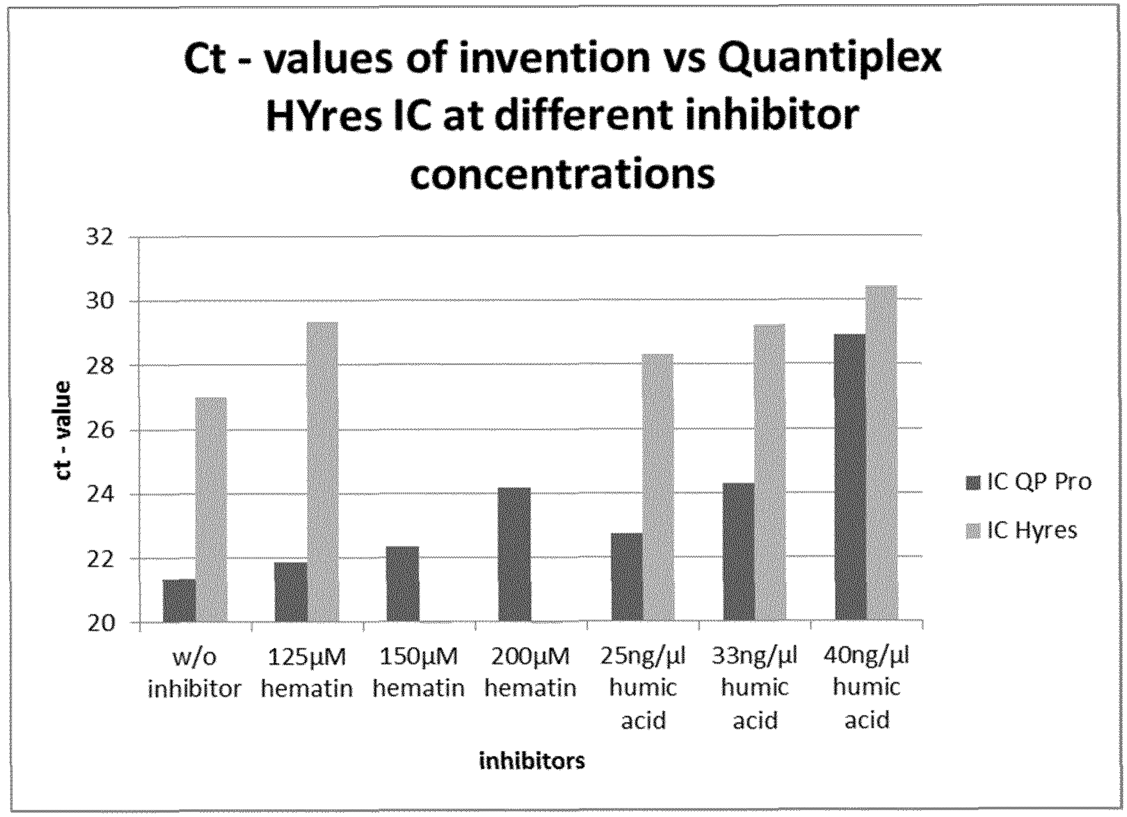

Specification includes a Sequence Listing.

(56) References Cited

OTHER PUBLICATIONS

F. Di Pasquale et al. "Analysis and interpretation of difficult samples—The interaction of a DNA quantification kit with the right STR assay may facilitate processing of critical trace material," Forensic Science International: Genetics Supplement Series, 2015, pp. e407-e408. vol. 5, Elsevier Ireland, Ltd., Ireland; Cited in ISR.

W. Hudlow et al. "A quadruplex real-time qPCR assay for the simultaneous assessment of total human DNA, human male DNA, DNA degradation and the presence of PCR inhibitors in forensic samples: A diagnostic tool for STR typing," Forensic Science International: Genetics, 2008, pp. 108-125, vol. 2, Elsevier Ireland Ltd. Ireland; Cited in ISR.

* cited by examiner

A

INTERNAL AMPLIFICATION CONTROL

A substitute sequence listing in ASCII format was submitted electronically via EFS-Web to replace a previously submitted sequence listing. The substitute sequence listing has a file name of "QIA-45489-Substitute_Sequence_Listing.txt", a creation date of June May 8, 2019, and a size of 1,626 bytes. The substitute sequence listing filed via EFS-Web is part of the specification and is hereby incorporated in its entirety by reference herein.

Molecular biology techniques are widely used in genotyping applications and other areas such as biological research, forensic and diagnostic applications, including human identification and paternity testing and for diagnosis of infectious diseases or chimera analysis after allogeneic bone marrow transplantation as well the detection of genetic diseases and cancer. The most commonly used technique is the polymerase chain reaction (PCR) that allows the researchers to amplify the desired DNA requiring only tiny amounts of sample.

Forensic workflow schemes entail the amplification of so called short tandem repeat (STR) markers. These markers are genetic elements of variable lengths that are characterized by short repetitive sequence motifs and are used in combination with other STR loci in order to obtain a genetic fingerprint of an individual. This information can be further used to accurately identify or eliminate a suspect by comparing this fingerprint with evidence from the crime scene.

After amplification, the resulting PCR products are labelled using fluorescent dyes and the technique of capillary electrophoresis (CE) is employed to separate said amplification products according to their molecular size. The fluorescent signals are represented as peaks in the electropherogram. In another embodiment, the primers are already labelled.

However, such analyses are hampered by several practical issues that prevent accurate genotyping. At the level of the template, possible degradation of the sample complicates efficient amplification of the target sequence. Further, naturally occurring compounds such as hematin or humic acid are potent inhibitors of PCR reactions. Since forensic samples are usually only available in very small quantities, the extent of possible troubleshooting in order to obtain a conclusive result is very limited.

Current means to provide an internal amplification control are hampered by non-specific binding that complicates subsequent analysis and do not allow for the distinction of the presence of inhibitors which they fail to report template degradation which may not be detected.

Therefore, there is a need for a system that allows the researcher to differentially identify said problems in amplification and detection experiments.

BRIEF DESCRIPTION OF THE INVENTION

The invention addresses the technical problems described above by means of an internal amplification control consisting of a set of primers and a template.

The invention relates to a method for evaluating the amplification efficiency and/or the presence of inhibitors and/or degradation and/or performing a quantification of a nucleic acid in a real-time amplification reaction comprising:

a. optionally amplifying in a reaction composition a first target nucleic acid using a first primer pair in a real-time amplification reaction, b. amplifying in said reaction composition one or more second internal nucleic acid control templates (IC) with a length of between 50 and 2000 nucleotides, wherein the second nucleic acid has a sequence selected from the group of:

i. SEQ ID NO. 1 or a sequence that differs by no more than 15% therefrom, ii. a reverse complement of SEQ ID NO. 1 or a sequence that differs by no more than 15% therefrom, iii. a sequence or a reverse complement thereof comprising the final 18 to 30 3'-nucleotides of SEQ ID NO. 1 at its terminal 3'-end and the final 18 to 30 5'-nucleotides of SEQ ID NO. 1 at its terminal 5'-end, or terminal ends that differ by no more than 15% from SEQ ID NO. 1, wherein between these terminal 3'-ends and 5'-ends the nucleic may have any nucleotide sequence and is between about 30 and about 1950 nucleotides in length.

In certain embodiments smaller amplification products in particular 200 bp to 600 bp are preferred. Herein, we refer sometimes to base pairs (bp) and some times to nucleotides both having the same meaning herein.

The invention further relates to a nucleic acid with a sequence, a. according to SEQ ID NO. 1 b. with a sequence that differs by no more than 15% therefrom, c. with a reverse complement sequence of SEQ ID NO. 1 or a sequence that differs by no more than 15% therefrom or, d. with a sequence or a reverse complement thereof comprising the final 18 to 30 3'-nucleotides of SEQ ID NO. 1 at its terminal 3'-end and the final 18 to 30 5'-nucleotides of SEQ ID NO. 1 at its terminal 5'-end, or terminal ends that differ by no more than 5% from SEQ ID NO. 1, wherein between these terminal 3'-ends and 5'-ends the nucleic may have any nucleotide sequence and is between about 30 and about 1950 nucleotides in length.

It also relates to an oligonucleotide with a sequence according to SEQ ID NO. 2, SEQ ID NO. 3, SEQ ID NO. 4 or the reverse complement thereof or at least containing the first 15 nucleotides in common with those according to SEQ ID NO. 2, 3 and 4, as well as a kit with IC and oligonucleotides.

DETAILED DESCRIPTION OF THE INVENTION

A "primer" herein refers to an oligonucleotide comprising a sequence that is complementary to a nucleic acid to be amplified or transcribed ("template"). During replication, a polymerase attaches nucleotides to the 3'-OH end of the primer complementary to the respective nucleotides of the template.

Herein, "STR" refers to short tandem repeats. Herein, "NGS" refers to Next Generation Sequencing.

The invention relates to a method for evaluating the amplification efficiency and/or the presence of inhibitors and/or degradation and/or performing a quantification of a nucleic acid in a real-time amplification reaction comprising:

a. optionally amplifying in a reaction composition, a first target nucleic acid using a first primer pair in a real-time amplification reaction, b. amplifying in said reaction composition one or more second internal nucleic acid control templates (IC) with a length of between 50 and 2000 nucleotides, preferably with a length of 200 nucleotides to 600 nucleotides, wherein the second nucleic acid has a sequence selected from the group of:
   i. SEQ ID NO. 1 or a sequence that differs by no more than 15% therefrom,
   ii. a reverse complement of SEQ ID NO. 1 or a sequence that differs by no more than 15% therefrom,
   iii. a sequence or a reverse complement thereof comprising the final 18 to 30 3'-nucleotides of SEQ ID NO. 1 at its terminal 3'-end and the final 18 to 30 5'-nucleotides of SEQ ID NO. 1 at its terminal 5'-end, or terminal ends that differ by no more than 5% from SEQ ID NO. 1, wherein between these terminal 3'-ends and 5'-ends the nucleic may have any nucleotide sequence and is between about 30 and about 1950 nucleotides in length.

Preferably the IC amplification product is detected with a probe according to SEQ ID NO. 4.

The invention further relates to a nucleic acid with a sequence, a. according to SEQ ID NO. 1
b. with a sequence that differs by no more than 15% therefrom,
c. with a reverse complement sequence of SEQ ID NO. 1 or a sequence that differs by no more than 15% therefrom or,
d. with a sequence or a reverse complement thereof comprising the final 18 to 30 3'-nucleotides of SEQ ID NO. 1 at its terminal 3'-end and the final 18 to 30 5'-nucleotides of SEQ ID NO. 1 at its terminal 5'-end, or terminal ends that differ by no more than 5% from SEQ ID NO. 1, wherein between these terminal 3'-ends and 5'-ends the nucleic may have any nucleotide sequence and is between about 30 and about 1950 nucleotides in length.

In the context of the present invention, the nucleic acid may have a sequence according to one of the aforementioned alternatives a-d.

It also relates to an oligonucleotide with a sequence according to SEQ ID NO. 2 or SEQ ID NO. 3 or the reverse complement thereof or at least containing the first 15 nucleotides in common with those according to SEQ ID NO. 2 and 3, as well as a kit with IC and oligonucleotides.

It also relates to an oligonucleotide with a sequence according to SEQ ID NO. 4 or the reverse complement thereof or at least containing the first 15 nucleotides in common with those according to SEQ ID NO. 4, as well as a kit with IC and oligonucleotides according to SEQ ID NO. 2, 3 and 4.

As used herein, the term "first 15 nucleotides" refers to the first 15 nucleotides starting from the 3'-end of said oligonucleotide according to the invention.

As used herein, the expression "sequence that differs by no more than 15% therefrom" refers to the degree of identity (percent identity) between a given query sequence, i.e. SEQ ID NO. 1, and a subject sequence. The determination of percent identity between two sequences is accomplished using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program, score=100, word length=12, to obtain percent identity between nucleotide sequences. BLAST protein searches are performed with the BLASTP program, score=50, word length=3, to obtain percent identity between amino acid sequences. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

As used herein, the term "about" refers to +/−5 nucleotides of a defined value and/or range.

As used herein, the term "terminal 3'-end" and "terminal 5'-end" refers to the nucleotide position at the 3'- and 5'-end of a nucleic acid, respectively. Accordingly, the term "final 18 to 30 3'- or 5'-nucleotides of SEQ ID NO. 1" refers to the terminal 18 to 30 nucleotides counted from the first nucleotide positioned at 3'- or 5'-end of the nucleic acid sequence SEQ ID NO. 1.

More specifically, the present invention encompasses at least one internal nucleic acid control template (IC) according to SEQ ID NO. 1, primers according to SEQ ID NO. 2 and 3 and a probe according to SEQ ID NO. 4 for using in method for quantifying and/or detecting a nucleic acid in a quantitative real-time PCR reaction.

In particular, the method relates to the use of an internal control nucleic acid and its amplification as an internal control.

The amplification methods will comprise buffers, dNTPs or NTPs in addition to the enzymes required.

As used herein, the term "dNTP" refers to deoxyribonucleoside triphosphates. Non-limiting examples of such dNTPs are dATP, dGTP, dCTP, dTTP, dUTP, which may also be present in the form of labelled derivatives, for instance comprising a fluorescence label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methylcytosine, pseudouridine, dihydrouridine, 5-methylcytidine. Furthermore, ddNTPs of the above-described molecules are encompassed in the present invention.

As used herein, the term "NTP" refers to ribonucleoside triphosphates. Non-limiting examples of such NTPs are ATP, GTP, CTP, TTP, UTP, which may also be present in the form of labelled derivatives, for instance comprising a fluorescent label, a radioactive label, a biotin label.

Preferably, when quantifying nucleic acids quantitative real-time PCR (rtPCR) is used.

In one embodiment, the internal nucleic acid template or the one or more internal nucleic acid templates are artificial nucleic acid templates. In an alternative embodiment, the internal nucleic acid template or the one or more internal nucleic acid templates consist of a sequence of an organism, which is different than the origin or suspected origin of the sample nucleic acid to be analyzed. In a preferred embodiment, the internal nucleic acid template or the one or more internal nucleic acid templates consist of a sequence with a very low identity to sequences in the sample. In a preferred embodiment, the internal nucleic acid template or templates have been generated using a random algorithm. In a more preferred embodiment the internal nucleic acid template or templates is similar to that of SEQ ID NO. 1.

In a preferred embodiment, the internal nucleic acid template or templates have a length between 70 and 2000 nucleotides. In a preferred embodiment, the internal nucleic acid template or templates have a length between 150 and 1500 nucleotides. In a more preferred embodiment the internal nucleic acid template or templates have a length between 150 and 1000 nucleotides. In an even more preferred embodiment the internal nucleic acid template or templates have a length between 200 and 500 nucleotides.

More preferably, the internal nucleic acid template or templates have a length between 50 and 2000 nucleotides. In a preferred embodiment, the internal nucleic acid template or templates have a length between 50 and 1500 nucleotides. In a more preferred embodiment the internal nucleic acid template or templates have a length between 50 and 1000 nucleotides. In an even more preferred embodiment the internal nucleic acid template or templates have a length between 50 and 500 nucleotides.

The IC may be prepared using synthesis by chemistry, PCR or even a plasmid. The amount of IC in each reaction is important. It is between 100.000 and 6.5 Mio. copies, preferably between 200.000 and 4 Mio. copies, more preferably between 300.000 and 3 Mio. copies and most preferably between 500.000 and 2.6 Mio. copies. Often, 650.000 copies were used per reaction which was found to be ideal.

The primer and probe concentrations are likewise important. Ideally, each primer and probe has a concentration of 0.05 μM to 0.35 μM, better 0.85 μM to 0.3 μM, ideally 0.15 μM to 0.25 μM, and best around 0.2 μM (+/−5-20%).

Preferably, the method of the invention is a real-time PCR reaction. The system herein comprises the IC (SEQ ID NO. 1), primers (SEQ ID NO. 2 and 3) and the detection probe (SEQ ID NO. 4). This system is preferably used in a quantitative real-time PCR. A real-time polymerase chain reaction is a laboratory technique of molecular biology based on the polymerase chain reaction (PCR). It monitors the amplification of a targeted DNA molecule during the PCR, i.e. in real-time, and not at its end, as in conventional PCR. Real-time PCR can be used quantitatively (quantitative real-time PCR), semi-quantitatively, i.e. above/below a certain amount of DNA molecules (Semi quantitative real-time PCR). Two common methods for the detection of PCR products in real-time PCR are: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence. The Minimum Information for Publication of Quantitative Real-Time PCR Experiments (MIQE) guidelines propose that the abbreviation qPCR be used for quantitative real-time PCR and that RT-qPCR be used for reverse transcription-qPCR. The acronym "RT-PCR" commonly denotes reverse transcription polymerase chain reaction and not real-time PCR, but not all authors adhere to this convention.

During PCR, the amount of DNA theoretically doubles with every cycle. After each cycle, the amount of DNA is twice what it was before.

The method according to the invention can be combined also with the use of a multi copy locus within the genome for further quantification, wherein the multicopy locus ideally is not a repetitive element for detecting and/or quantifying the nucleic acids of said genome. In one embodiment, the use of said multi copy locus is intended for detecting and/or quantifying nucleic acids according to the herein cited methods or for analyzing the status of degradation of human DNA. Forensic scientists often deal with case-work samples from different sources. These samples can be degraded due to different factors such as environmental stress. Therefore, the internal nucleic acid control template (IC) according to the invention can additionally be used in a STR reaction to provide with information about the degradation status of DNA sample as well as information on the presence of inhibitors (see FIG. 3B).

The present invention also encompasses the use of a nucleic acid with a sequence, a. according to SEQ ID NO. 1
b. with a sequence that differs by no more than 15% therefrom,
c. with a reverse complement sequence of SEQ ID NO. 1 or a sequence that differs by no more than 15% therefrom or,
d. with a sequence or a reverse complement thereof comprising the final 18 to 30 3'-nucleotides of SEQ ID NO. 1 at its terminal 3'-end and the final 18 to 30 5'-nucleotides of SEQ ID NO. 1 at its terminal 5'-end, or terminal ends that differ by no more than 5% from SEQ ID NO. 1, wherein between these terminal 3'-ends and 5'-ends the nucleic may have any nucleotide sequence and is between about 30 and about 1950 nucleotides in length, and/or an oligonucleotide with a sequence according to SEQ ID NO. 2 or SEQ ID NO. 3 or the reverse complement thereof or at at least containing the first 15 nucleotides in common with those according to SEQ ID NO. 2 and 3 or an oligonucleotide with a sequence according to SEQ ID NO. 4 or the reverse complement thereof, or at least sharing 95% sequence identity thereto or to the reverse complement in a real time PCR reaction for the detection and/or quantification of inhibitors in said reaction and/or for the detection and/or quantification of a nucleic acid in a STR reaction.

As used herein, the term "STR reaction" refers to multiplex system used to identify specific short tandem repeats (STRs) in a DNA sample.

The invention also relates to a human DNA degradation marker evaluation system with higher sensitivity and accuracy than state of the art methods.

Using real-time PCR techniques, fluorescence is detected and measured in the real-time PCR thermocycler, and its geometric increase corresponding to exponential increase of the product is used to determine the threshold cycle (Ct) in each reaction.

The unknown and each of the standards are amplified in separate tubes. A standard curve (plot of Ct value/crossing point against log of amount of standard) is generated using different dilutions of the standard. The Ct value of the unknown samples is compared with the standard curve, allowing calculation of the initial amount of the target. It is important to select an appropriate standard for the type of nucleic acid to be quantified. To generate a standard curve, at least 5 different amounts of the standard should be quantified, and the amount of unknown target should fall within the range of the standard curve. Hence, in one embodiment also the above quantification steps are performed.

Labelling systems comprise rare earth cryptates or rare earth chelates in combination with a fluorescence dye or chemiluminescence dye, in particular a dye of the cyanine type. In the context of the present invention, fluorescence based assays comprise the use of dyes, which may for instance be selected from the group comprising FAM (5- or 6-carboxyfluorescein), VIC, NED, Fluorescein, Fluorescein-isothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like. In the context of the present invention, chemiluminescence based assays comprise the use of dyes, based on the physical principles described for chemiluminescent materials in Kirk-Othmer, Encyclopedia of chemical technology, 4th ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridinium esters.

The oligonucleotides are made of nucleotides. Herein, "nucleotide" is defined herein to include both nucleotides and nucleosides. Nucleosides, as for nucleotides, comprise a purine or pyrimidine base linked glycosidically to ribose or deoxyribose, but they lack the phosphate residues which would make them a nucleotide. Synthetic and naturally occurring nucleotides, prior to their modification at the 3' sugar hydroxyl, are included within the definition.

Preferably, the first target nucleic acid is a short tandem repeat (STR) marker and the method is performed in the context of genotyping.

Ideally, a defined amount of IC nucleic acid is added to the reaction and the expected amplification product amount usually obtained in the absence of an amplification inhibitor is compared to the product amount obtained in the reaction.

Ideally, the primers used for amplifying the internal nucleic acid control templates (IC) have a nucleotide sequence according to SEQ ID NO. 2 and 3, or the reverse complement thereof or at least have the first fifteen 3'-prime nucleotides in common with the sequences according to SEQ ID NO. 2 and 3.

Oligonucleotide primers may be prepared using any suitable method, such as, for example, the phosphotriester and phosphodiester methods or automated embodiments thereof. In one such automated embodiment diethyl phosphoramidites are used as starting materials and may be synthesized as described by Beaucage et al. (1981) Tetrahedron Letters 22:1859-1862. One method for synthesizing oligonucleotides on a modified solid support is described in U.S. Pat. No. 4,458,006. It is also possible to use a primer, which has been isolated from a biological source (such as a restriction endonuclease digest). Preferred primers have a length of about 6-100 bases, more preferably about 20-50, most preferably about 20-40 bases.

The invention also relates to nucleic acid (IC) with a sequence, i) according to SEQ ID NO. 1, ii) with a sequence that differs by no more than 15% therefrom, iii) with a reverse complement sequence of SEQ ID NO. 1 or a sequence that is differs by no more than 15% therefrom or, iv) with a sequence or a reverse complement thereof comprising the final 18 to 30 3'-nucleotides of SEQ ID NO. 1 at its terminal 3'-end and the final 18 to 30 5'-nucleotides of SEQ ID NO. 1 at its terminal 5'-end, or terminal ends that differ by no more than 5% from SEQ ID NO. 1, wherein between these terminal 3'-ends and 5'-ends the nucleic may have any nucleotide sequence and is between about 30 and about 1950 nucleotides in length. Preferably the length is between 200 bp (or nucleotides) and 600 bp (or nucleotides).

The invention also relates to an IC which is not identical but shares at least, 80%, 85%, 90%, better 95% sequence identity with SEQ ID NO. 1 or its reverse complement.

The IC the inventors have devised is as follows:

SEQ ID NO. 1

5' GTAGCTCCATAATCAGAAGATGCGctaccgtacacaacggcggtttaa actttgtagacctcacgcggctgctcaggtcttgcgcatcccatacttcac atggacggaaagctgtgggtttgtatcgataagccgtaggttcctaggatc gagtcacccaaacaacttcgagagctcttctcaccaaccctttgaactccg aaatgccgtgaacacatccccttagttggcattggtctactaaccgagtat cgtacaaagcgagacaggtctggcccctactgcttggatgcgaactaacag tgttcctatatccgtttatactgtggtcgatttcgaaccgatatctcaaag agagcgccggcagagccttagtatcggaactggcgagtgtgtttgggtgag gaCTATTATGTGGTTGGAGTAGAGCGAAT 3'

The invention also relates to an oligonucleotide with a sequence according to SEQ ID NO. 2 or SEQ ID NO. 3 or the reverse complement thereof or at least containing the first 15 3'-prime nucleotides in common with those according to SEQ ID NO. 2 and 3.

The oligonucleotide primers the inventors have created are as follows:

SEQ ID NO. 2

5' gtagctccataatcagaagatgcg 3'

SEQ ID NO. 3

5' attcgctctactccaaccacataatag 3'

The probe the inventors have created is as follows:

SEQ ID NO. 4

5' tccgatactaaggctctgccggcgct 3'

The invention also relates to an oligonucleotide with a sequence according to SEQ ID NO. 4 or the reverse complement thereof, or at least sharing 95% sequence identity thereto or to the reverse complement.

The invention relates to the use of the nucleic acid and/or an oligonucleotide in a real-time amplification reaction for the detection and/or quantification of inhibitors in the reaction and/or for the quantification of a nucleic acid in said reaction.

It also relates to a kit for evaluating the amplification efficiency and/or the presence of inhibitors and/or degradation in an amplification reaction, comprising i. a nucleic acid according to claim with SEQ ID NO. 1 and/or a ii. oligonucleotides according to SEQ ID NO. 2, 3 or 4.

The nucleic acid according to the kit for evaluating the amplification efficiency and/or the presence of inhibitors and/or degradation in an amplification reaction can alternatively or additionally comprises i. a sequence that differs by no more than 15% from SEQ ID NO. 1, ii. a reverse complement sequence of SEQ ID NO. 1 or a sequence that is differs by no more than 15% therefrom or, iii. a sequence or a reverse complement thereof comprising the final 18 to 30 3'-nucleotides of SEQ ID NO. 1 at its terminal 3'-end and the final 18 to 30 5'-nucleotides of SEQ ID NO. 1 at its terminal 5'-end, or terminal ends that differ by no more than 5% from SEQ ID NO. 1, wherein between these terminal 3'-ends and 5'-ends the nucleic may have any nucleotide sequence and is between about 30 and about 1950 nucleotides in length, preferably between 200 and 600 nucleotides in length.

The oligonucleotide according to the kit for evaluating the amplification efficiency and/or the presence of inhibitors and/or degradation in an amplification reaction can alternatively or additionally comprises i. a reverse complement sequence of SEQ ID NO. 2 or SEQ ID NO. 3 or at least containing the first 15 nucleotides in common with those according to SEQ ID NO.2 and SEQ ID NO. 3, and/or ii. a reverse complement sequence of SEQ ID NO. 4 or at least sharing 95% sequence identity thereto or to the reverse complement.

The method relates to one internal amplification product. This system makes use of a specific combination of (i) an IC template which is added to the quantitative real-time PCR in a defined amount (SEQ ID NO. 1), (ii) a specific primer set (SEQ ID NO. 2 and 3) as well as (iii) a probe for detection (SEQ ID NO. 4).

When one, e.g. only one genomic template and one IC are used, these amplification products are referred to herein as first and second amplification product.

The amplification may be a multiplex PCR. Multiplex PCR is for example used for the simultaneous detection of multiple marker genes and/or their polymorphisms, e.g. short tandem repeats (STRs) or deletion insertion polymorphisms (DIPS or Indels). Detection of the amplification products and their genotyping is usually carried out by multiple colour fluorescence detection after electrophoretic separation (e.g. capillary gel electrophoresis) in DNA sequencers. In real-time, quantitative multiplex PCR, the amplification of multiple target sequences can be monitored at the same time by simultaneous detection of fluorescence of different fluorescent dyes. The inventive system may be used to quantify nucleic acids precisely prior to STR analysis or prior to NGS analysis. Both require a precise titration of the DNA amount used.

The amplification reaction is preferably selected from the group comprising real-time polymerase chain reaction (PCR), real-time ligase chain reaction (LCR), transcription-based amplification system (TAS), nucleic acid sequence based amplification (NASBA), rolling circle amplification (RCA), transcription-mediated amplification (TMA), self-sustaining sequence replication (3SR), QP amplification and (thermostable) helicase dependent amplification ((t)HAD). More preferably the amplification reaction is a real-time PCR. Most preferably, the amplification reaction is a multiplex real-time PCR, i.e. the amplification of more than one target nucleic acid sequence in a single tube, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 loci (target nucleic acid sequences) may be amplified simultaneously.

In a preferred embodiment, the invention relates to a method for evaluating the amplification efficiency and/or the presence of inhibitors and/or degradation in an amplification reaction, this may be done prior to an STR analysis or NGS analysis.

Analysis of the target amplification products and the internal control fragments allows for the differential identification of the presence of inhibitors or degradation of the sample.

The system is preferably used in a quantitative real-time PCR set-up. The relevant indices measured are primarily the Ct values. Given a certain amount of IC and certain Ct values can be expected. If the Ct values is higher, i.e. the signal appears only in later cycles, this shows inhibition of the reaction.

Examples

Ideally, the internal control in DNA quantification is a PCR system, which reliably is reporting the presence of PCR inhibitors in the sample while PCR systems for quantification function as stable as possible. Human DNA isolated from various sources has to be assessed in terms of quantity, quality and integrity prior to further forensic testing e.g. STR analyses, next-generation-sequencing. These are complex systems that require a defined range of input DNA and template quality to perform accurately, therefore DNA-quantification is an important step within the forensic workflow. Many commercial available kits for DNA quantification contain an internal PCR amplification control (IC). The IC in many commercially available DNA quantification kits suffer from poor correlation to the inhibitor resistance of new generation STR-Kits, or fail report the presence these inhibitors in a gradational manner. Examples of inhibitor sensitivity in quantification reactions are shown in FIG. 2 with two commercially available kits. The Quantifiler TRIO kit fails to report any hematin concentration higher than 125 μM, while the Promega PowerQuant kit shows virtual no reaction for humic acid concentrations tested and only a slight increase in Ct values of 0.6 for 200 μM of hematin, giving a poor resolution of inhibitor presence in the sample. We could achieve a high stability of the internal control to high concentrations of inhibitors with a gradational increase of Ct values reporting inhibitor presence (FIG. 1; 125 μM, 150 μM and 200 μM of hematin and 25 ng/μl, 33 ng/μl and 40 ng/μl of humic acid), which perfectly fits the inhibitor resistance of the Next generation STR-Kits.

The typical forensic workflow suggests the quantification of the DNA before the STR reaction is carried out. This is done to determine how much DNA was obtained from a sample, e.g. collected from a crime scene, and how much of this DNA should be used in an STR reaction. The typical STR reaction works optimally in a certain range of template DNA and the analysis is very labor-intensive, therefore methodologies are needed that ensure a very high success rate. Therefore, it is a real advantage that the present invention enables the user not only to surely quantify the amount of DNA present but also to assess the absence of inhibitors, which could compromise the STR-reaction result, which would result in failure or loss of valuable sample material.

The performance of the internal nucleic acid control templates (IC) according to the invention with a length of between 50 and 2000 nucleotides is amazing. It is sensitive to the presence of inhibitors but is able to report the presence these inhibitors in a gradational manner with an excellent correlation to inhibitor resistance of new generation STR-kits. It has been found that the IC with 200 to 600 nucleotides in length works very well.

Some of the new generations of STR kits demonstrate increased inhibitor resistance as kits introduced earlier.

These new STR kits have been further optimized to provide higher resistance to PCR inhibitors, which also provides new requirements to the DNA quantification methodology, by providing an IC that only reports levels of inhibition that are significant for the success of the subsequent STR reaction.

The IC the inventors have devised is as follows:

SEQ ID NO. 1

5' GTAGCTCCATAATCAGAAGATGCGctaccgtacacaacggcggtttaa
actttgtagacctcacgcggctgctcaggtcttgcgcatcccatacttcac
atggacggaaagctgtgggtttgtatcgataagccgtaggttcctaggatc
gagtcacccaaacaacttcgagagctcttctcaccaaccctttgaactccg
aaatgccgtgaacacatccccttagttggcattggtctactaaccgagtat
cgtacaaagcgagacaggtctggcccctactgcttggatgcgaactaacag
tgttcctatatccgtttatactgtggtcgatttcgaaccgatatctcaaag
agagcgccggcagagccttagtatcggaactggcgagtgtgtttgggtgag
gaCTATTATGTGGTTGGAGTAGAGCGAAT 3'

The primers the inventors have created are as follows:

SEQ ID NO. 2

5' gtagctccataatcagaagatgcg 3'

SEQ ID NO. 3

5' attcgctctactccaaccacataatag3'

The probe the inventors have created is as follows:

SEQ ID NO. 4

5' tccgatactaaggctctgccggcgct 3'

Figure Captions

Figure 2:
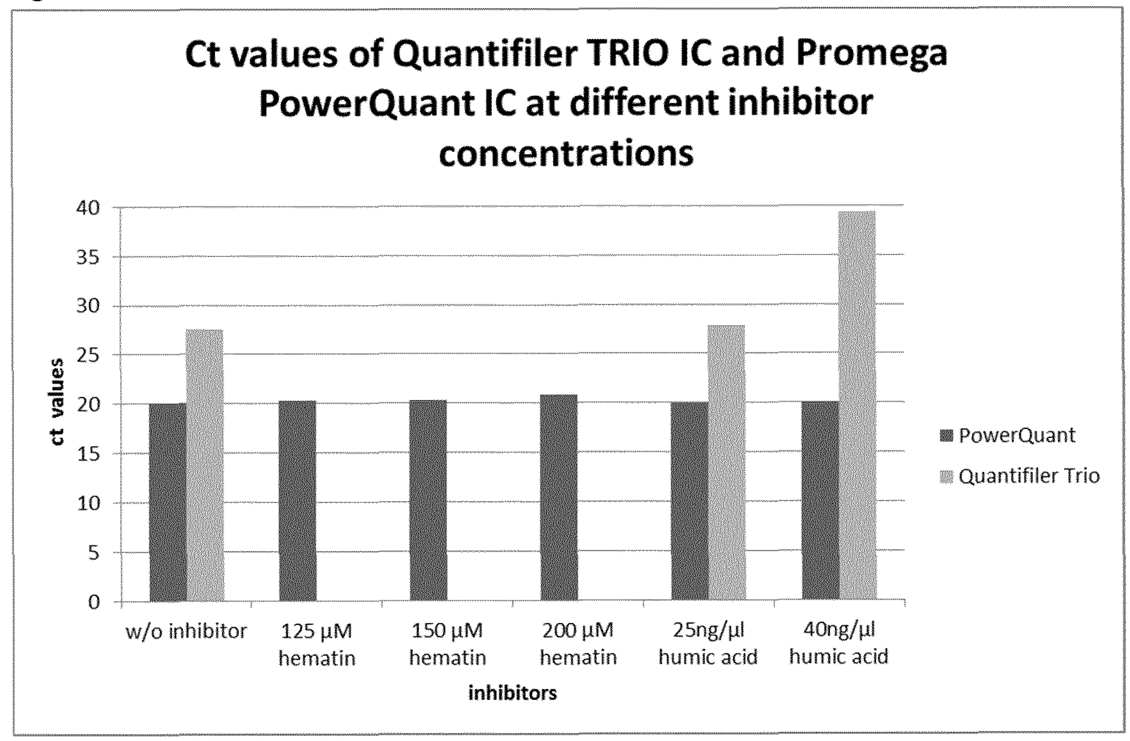

FIG. 1 shows a comparison of the invention (IC) with the internal control from the QIAGEN Quantiplex HYres kit. When humic acid was applied to PCR reaction, both systems showed sensitivity towards the tested concentrations of 25 ng/μL, 33 ng/μL and 40 ng/μL. The invention (IC) reported the presence of inhibitor more gradually by higher Ct value differences than the internal control of the Quantiplex HYres kit. However, when hematin was tested with concentration of 125 ng/μL, 150 ng/μL and 200 ng/μL the Quantiplex HYres internal control failed to amplify at all at concentrations higher than 125 ng/μL, whereas the invention shows a gradually increase in Ct values providing an excellent correlation to inhibitor resistance of new generation STR-kits.

FIG. 2 shows a comparison of the Applied Biosystems Quantifiler TRIO kit IC with the Promega PowerQuant IC. When hematin was applied to PCR reaction, the Quantifiler TRIO IC failed to detect hematin concentrations above 125 μM while the PowerQuant IC reported only the highest concentration applied (200 μM). When humic acid was applied the PowerQuant IC failed to report the concentrations tested, while the Quantifiler TRIO reported the tested concentrations of 25 ng/μL and 40 ng/μL of humic acid.

Figure 3:
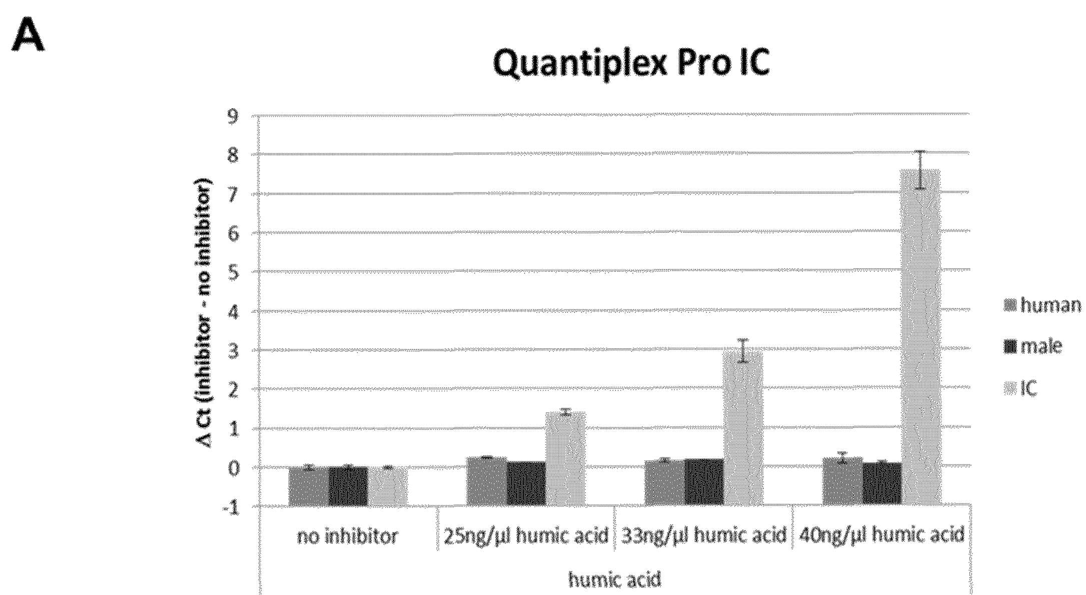
Figure 3B:
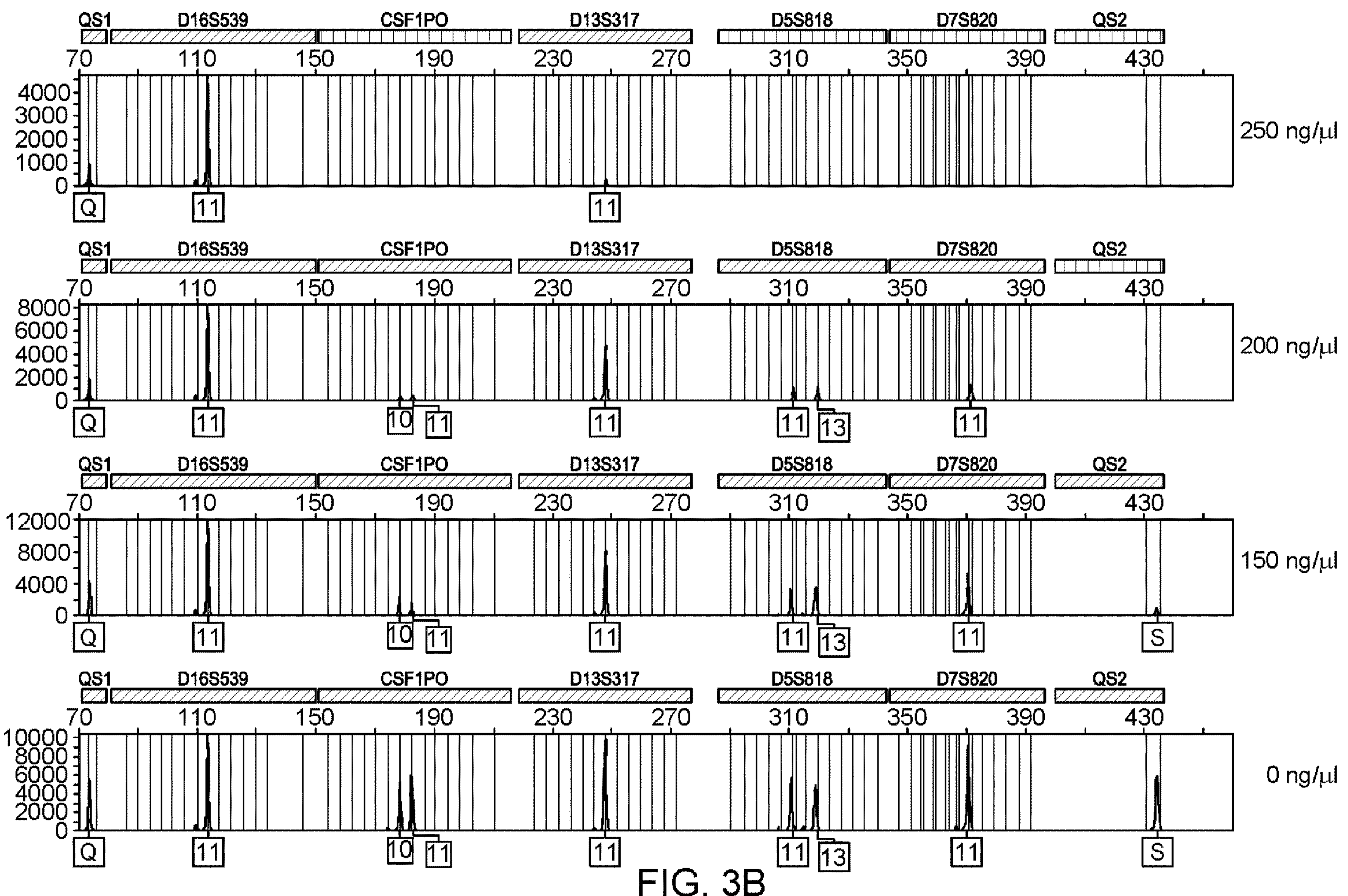

FIG. 3 shows the response of IC to inhibitors correlates to STR QS Kit results. In particular, FIG. 3 shows the response of the invention (IC) in combination with other quantification targets to different concentration of humic acid. A) Performance of the Investigator Quantiplex Pro Kit IC with simulated humic acid inhibition. The internal control reports the presence of the inhibitor (ΔCt) while the quantification is reliable up to a concentration of 40 ng/μl. The figure shows the average ΔCt±standard deviation. B) This corresponds to a concentration in the STR reaction of 250 ng/μl, if the maximum template volume of 15 μl is applied. The Investigator 24plex QS Kit shows resistance to humic acid of up to 200 ng/μl (final concentration in the reaction), while the quality sensor (QS) drops out and reports inhibitor presence with comparable performance as the IC in the Quantiplex Pro Kit. This demonstrates the benefit of using the same template as internal control (IC) in real time PCR quantification kits and STR kits in order to report the presence of inhibitors in the samples in a more consistent and meaningful manner.

The invention claimed is:

1. A method for evaluating the amplification efficiency and/or the presence of inhibitors and/or degradation and/or performing a quantification of a target nucleic acid in a reaction composition in a real-time amplification reaction, the method comprising:

(a) amplifying the target nucleic acid in the reaction composition in the real-time amplification reaction, (b) amplifying one or more internal nucleic acid control templates (IC) with a length of between 50 and 2000 nucleotides in the reaction composition in the real-time amplification reaction using a set of primers; and (c) detecting an amplification product of the one or more internal nucleic acid control templates (IC) using an oligonucleotide probe;

wherein each of the one or more internal nucleic acid control templates (IC) has a sequence selected from the group of:

SEQ ID NO. 1, or a sequence that differs by no more than 15% from SEQ ID NO. 1, and (ii) a reverse complement of SEQ ID NO. 1, or a sequence that differs from the reverse complement of SEQ ID NO. 1 by no more than 15%, wherein the set of primers used for amplifying the one or more internal nucleic acid control templates (IC) have a nucleotide sequence according to SEQ ID NO. 2 and SEQ ID NO. 3, or at least have the first fifteen 3' nucleotides in common with the sequences according to SEQ ID NO. 2 and SEQ ID NO. 3, and wherein the oligonucleotide probe used for detecting the amplification product of the one or more internal nucleic acid control templates (IC) has a sequence according to SEQ ID NO. 4.

2. The method according to claim 1, wherein the real-time amplification reaction is a real-time PCR reaction.

3. The method according to claim 1, wherein, in order to evaluate the presence of inhibitors, a defined amount of the one or more internal nucleic acid control templates (IC) is added to the reaction composition and the amplification product amount of the one or more internal nucleic acid control templates (IC) obtained in the real-time amplification reaction is compared to the amplification product amount of the one or more internal nucleic acid control templates (IC) that would be expected to be obtained in the real-time amplification reaction in an absence of an amplification inhibitor.

4. A method for evaluating the amplification efficiency and/or the presence of inhibitors and/or degradation in a reaction composition that includes a target nucleic acid in a real-time amplification reaction, the method comprising:

(a) optionally amplifying the target nucleic acid in the reaction composition in the real-time amplification reaction, (b) amplifying one or more internal nucleic acid control templates (IC) with a length of between 50 and 2000 nucleotides in the reaction composition in the real-time amplification reaction using a set of primers; and (c) detecting an amplification product of the one or more internal nucleic acid control templates (IC) using an oligonucleotide probe;

wherein each of the one or more internal nucleic acid control templates (IC) has a sequence selected from the group of:

SEQ ID NO. 1, or a sequence that differs by no more than 15% from SEQ ID NO. 1, and (ii) a reverse complement of SEQ ID NO. 1, or a sequence that differs from the reverse complement of SEQ ID NO. 1 by no more than 15%, wherein the set of primers used for amplifying the one or more internal nucleic acid control templates (IC) have a nucleotide sequence according to SEQ ID NO. 2 and SEQ ID NO. 3, or at least have the first fifteen 3' nucleotides in common with the sequences according to SEQ ID NO. 2 and SEQ ID NO. 3, and wherein the oligonucleotide probe used for detecting the amplification product of the one or more internal nucleic acid control templates (IC) has a sequence according to SEQ ID NO. 4.

5. The method according to claim 4, wherein the real-time amplification reaction is a real-time PCR reaction.

6. The method according to claim 4, wherein, in order to evaluate the presence of inhibitors, a defined amount of the one or more internal nucleic acid control templates (IC) is added to the reaction composition and the amplification product amount of the one or more internal nucleic acid control templates (IC) obtained in the real-time amplification reaction is compared to the amplification product amount of the one or more internal nucleic acid control templates (IC) that would be expected to be obtained in the real-time amplification reaction in an absence of an amplification inhibitor.

* * * * *

UNITED STATES PATENT AND TRADEMARK OFFICE

CERTIFICATE OF CORRECTION

PATENT NO. : 11,345,952 B2
APPLICATION NO. : 16/333143
DATED : May 31, 2022
INVENTOR(S) : Miroslav Vranes et al.

It is certified that error appears in the above-identified patent and that said Letters Patent is hereby corrected as shown below:

In the Claims

In Column 13, Line 49, add "(i)" before --SEQ ID NO. 1, or a sequences that differs by no more--

In Column 14, Line 57, add "(i)" before --SEQ ID NO. 1, or a sequences that differs by no more--

Signed and Sealed this
Sixteenth Day of August, 2022

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 434
<212> TYPE: DNA
<213> ORGANISM: Artificial Sequence
<220> FEATURE:
<223> OTHER INFORMATION: Internal nucleic acid control template

<400> SEQUENCE: 1

gtagctccat aatcagaaga tgcgctaccg tacacaacgg cggtttaaac tttgtagacc     60

tcacgcggct gctcaggtct tgcgcatccc atacttcaca tggacggaaa gctgtgggtt    120

tgtatcgata agccgtaggt tcctaggatc gagtcaccca aacaacttcg agagctcttc    180

tcaccaaccc tttgaactcc gaaatgccgt gaacacatcc ccttagttgg cattggtcta    240

ctaaccgagt atcgtacaaa gcgagacagg tctggcccct actgcttgga tgcgaactaa    300

cagtgttcct atatccgttt atactgtggt cgatttcgaa ccgatatctc aaagagagcg    360

ccggcagagc cttagtatcg gaactggcga gtgtgtttgg gtgaggacta ttatgtggtt    420

ggagtagagc gaat                                                      434


<210> SEQ ID NO 2
<211> LENGTH: 24
```

-continued

```
<212> TYPE: DNA
<213> ORGANISM: Artificial Sequence
<220> FEATURE:
<223> OTHER INFORMATION: Synthetic Primer

<400> SEQUENCE: 2

gtagctccat aatcagaaga tgcg                                    24


<210> SEQ ID NO 3
<211> LENGTH: 27
<212> TYPE: DNA
<213> ORGANISM: Artificial Sequence
<220> FEATURE:
<223> OTHER INFORMATION: Synthetic Primer

<400> SEQUENCE: 3

attcgctcta ctccaaccac ataatag                                 27


<210> SEQ ID NO 4
<211> LENGTH: 26
<212> TYPE: DNA
<213> ORGANISM: Artificial Sequence
<220> FEATURE:
<223> OTHER INFORMATION: Synthetic Probe

<400> SEQUENCE: 4

tccgatacta aggctctgcc ggcgct                                  26
```